(12) United States Patent
Watson et al.

(10) Patent No.: US 8,784,795 B2
(45) Date of Patent: Jul. 22, 2014

(54) METHODS FOR DETERMINING PERSONALIZED TREATMENT COMPOSITIONS FOR PROSTATE CANCER AND BREAST CANCER

(71) Applicant: Caldera Health Ltd., Auckland (NZ)

(72) Inventors: James D. Watson, Auckland (NZ); Richard Llewellyn Sydney Forster, Pukekohe (NZ)

(73) Assignee: Caldera Health Limited, Auckland (NZ)

( * ) Notice: Subject to any disclaimer, the term of this patent is extended or adjusted under 35 U.S.C. 154(b) by 0 days.

(21) Appl. No.: 13/935,355

(22) Filed: Jul. 3, 2013

(65) Prior Publication Data

US 2014/0010777 A1    Jan. 9, 2014

Related U.S. Application Data

(60) Provisional application No. 61/668,395, filed on Jul. 5, 2012.

(51) Int. Cl.
  *G01N 33/50* (2006.01)
  *A61K 31/497* (2006.01)
  *A61K 38/19* (2006.01)

(52) U.S. Cl.
  USPC .......................................... 424/85.1; 435/32

(58) Field of Classification Search
  None
  See application file for complete search history.

(56) References Cited

U.S. PATENT DOCUMENTS

| | | | |
|---|---|---|---|
| 7,358,046 B2 | 4/2008 | Kawabe et al. | |
| 7,678,552 B2 | 3/2010 | Kornblith | |
| 2009/0042225 A1* | 2/2009 | Kornblith | 435/7.92 |

OTHER PUBLICATIONS

Heppner et al. Tumor heterogeneity: biological implications and therapeutic consequences Cancer Metastasis Review. 1983; 2: 5-23.*
Haendler et al. Recent developments in antiandrogens and selective androgen receptor modulators. Molecular and Cellular Endocrinology. published online Jun. 16, 2011; 352:79-91.*
Dreicer et al. Phase II trial of GM-CSF + thalidomide in patients with androgen-independent metastatic prostate cancer. Urologic Oncology: Seminars and Original Investigations. 2005; 23: 82-86.*
Risk, Michael M.D., The Role of Immunotherapy in Prostate Cancer: An Overview of Current Approaches in Developement, Review in Urology, vol. 11, No. 1, pp. 16-27 (2009).
Sunami, Eiji et al., "Estrogen receptor and HER2/neu status affect epigenetic differences of trumor-related genes in primary breast tumors," Breast Cancer Research, vol. 10, No. 3, pp, 1-11 (Jan. 2008).

* cited by examiner

*Primary Examiner* — Vanessa L. Ford
*Assistant Examiner* — Sandra Dillahunt
(74) *Attorney, Agent, or Firm* — Janet Sleath; Speckman Law Group PLLC (57) ABSTRACT

The present disclosure provides methods for selecting a treatment composition, or therapy, for the treatment of a cancer, such as prostate or breast cancer, in a patient wherein the treatment composition includes administering a combination of at least two components selected from two different classes of compounds. Methods for treating a patient using the selected treatment composition are also provided, together with methods for monitoring the efficacy of the treatment composition during a treatment period.

15 Claims, 6 Drawing Sheets

METHODS FOR DETERMINING PERSONALIZED TREATMENT COMPOSITIONS FOR PROSTATE CANCER AND BREAST CANCER

REFERENCE TO RELATED APPLICATIONS

This application claims priority to U.S. provisional patent application No. 61/668,395, filed Jul. 5, 2012.

TECHNICAL FIELD

The present disclosure relates to methods for determining optimum therapeutic treatment including combinations of therapeutic compositions for individuals suffering from prostate cancer or breast cancer.

BACKGROUND

In many countries prostate cancer is the most common, or the second most common, cancer diagnosed in males. Similarly, breast cancer is the most common, or the second most common, cancer diagnosed in females in many countries. There are many common epidemiological, genetic, biochemical and mechanistic aspects of these two cancers. Incidence rates, lifetime risks, dietary factors (especially diets high in fat and low in fiber), death rates, ethnic trends and country of residence are among the common epidemiological features. In addition, steroid hormones play an important role in the pathogenesis of both cancers. Unless detected early, prostate and breast cancer may spread to the spine and bones of the patient, causing severe pain, bone frailty and death.

The same general range of treatment options exist for both prostate and breast cancers, namely surgery, radiation and hormone ablation/depletion. Hormone-ablation or depletion treatment (for example, blocking androgen production or activity) is frequently prescribed for metastatic cancers, however the cancer may become resistant to hormone ablation therapy and chemotherapy often becomes a final option for treatment. Life quality often deteriorates during chemotherapy and life expectancy is generally limited. One of the major side effects of chemotherapy is the destruction of the body's immune system.

Androgens, such as testosterone, are the key drivers of prostate cancer. The most convincing demonstration of androgen involvement is the dramatic reduction of prostate cancer risk in prepubertal castrates. The active metabolite of testosterone, dihydro-testosterone, is generated by the action of the enzyme 5α-reductase. In females, estrogen stimulates the growth of many breast cancers. Such cancers have estrogen receptors on the surface of their cells and are called estrogen receptor-positive (ER-positive) cancer. Breast cancer patients with ER-positive tumors generally have a more favorable prognosis than those with ER-negative tumors, and such patients can generally be successfully treated with hormonal therapies such as tamoxifen and aromatase inhibitors. In contrast, women with HER2 (human epidermal growth factor receptor)-positive breast cancer have a more aggressive disease and a higher risk that the disease will recur than women who do not have HER2-positive cancer.

Androgens and estrogens are steroid hormones which exert their actions by binding and activating transcription factors which form the steroid hormone receptor family. These transcription factors, in turn, regulate a large number of other genes. Steroid hormones with very different biological activities can be inter-converted by the action of enzymes. Tissues that were traditionally thought to be responsive to one class of such steroids are now known to contain receptors for other classes. For example, the breast has androgen receptors in addition to estrogen and progesterone receptors, and the prostate has estrogen and progesterone receptors in addition to testosterone receptors.

Blockade of hormone action (such as androgen or estrogen action) by pharmacological agents often confers primary protection against the cancer. Such pharmacological agents may directly kill the target prostate cancer or breast cancer cells, or may slow their growth rate or impair their metabolic activity. This can result in a partial and incomplete apoptotic state.

Pharmacological agents used in the treatment of cancers, such as prostate and breast cancers, include immune activators, such as interleukin 2 (IL2) which is a specific T cell growth factor, granulocyte-macrophage colony stimulating factor (GM-CSF; also known as sargramostim; trade name Leukine®), and granulocyte colony stimulating factor (G-CSF; also known as filgrastim; trade name Neupogen®). IL2 was initially used mainly as an in vitro stimulant in cancer therapy to augment specific CD8-positive T cell mediated anti-tumor immunity and activation of non-specific cytolytic effector cells, termed lymphokine-activated killer (LAK) cells. IL2 can induce the proliferation and expansion in number of tumor-reactive T cells in vitro, and T cells grown in culture with IL2 can be effective reagents in vivo for specific tumor therapy. T cells cultured long-term in vitro with IL2 are functionally limited in vivo without the administration of exogenous IL2. In contrast, T cells grown in vitro with specific antigen, as opposed to IL2, as the major stimulus for proliferation are able to proliferate rapidly in vivo, and distribute widely in host lymphoid organs. IL2 has negative side effects in vivo which limit its clinical use.

Both GM-CSF and G-CSF were initially developed for the rapid restoration of neurophils following whole body irradiation and for use in other disorders characterized by neutrophil deficiency. Administration of GM-CSF has been demonstrated to lead to long-term control of prostate cancer in a substantial number of patients (Rini et al., *J. Urol.* 2006, 175(6):2087-91).

The autologous cellular immunotherapy Provenge® (sipuleucel-T; Dendreon Corp., Seattle, Wash.) was recently approved in the US for treatment of asymptomatic or minimally symptomatic metastatic castrate resistant (hormone refractory) prostate cancer. In this therapy, white blood cells (primarily antigen presenting, or dendritic, cells) are isolated from the patient and incubated with a fusion protein comprising a fragment of prostatic acid phosphatase (PAP; known to be present in 95% of prostate cancers) chemically bound to GM-CSF. The resulting activated cells are then administered back to the patient. The activated dendritic cells have, as their primary function, the activation of cytotoxic CD8+ cells in the patient which then target and kill prostate cancer cells expressing PAP antigens. Only a patient's own dendritic cells can be used, due to the requirement for histocompatibility between the dendritic cells and specific CD8+ cytotoxic T cells. The recommended course of therapy for Provenge® is three complete doses, given at approximately 2-week intervals. The biggest drawback to this therapy is its high cost.

Filgrastim (G-CSF) is approved for use in cancer patients with bone marrow damage due to chemotherapy or radiotherapy. It has been shown that patients treated with filgrastim have fewer infections, less need for intravenous antibiotics, and shortened hospital stays compared to those who do not receive the drug. Filgrastim is often used in breast cancer treatments. Both GM-CSF and G-CSF have similar biological profiles, with G-CSF being the more potent stimulator of neutrophil regeneration.

Another therapeutic agent employed in the treatment of prostate cancer is ketoconazole, a synthetic drug that was originally developed as an antifungal agent. In a clinical trial, ketoconazole was shown to have a 50% response rate in hormone refractory prostate cancer. Significant side effects were reduced by reducing the dosage (Harris et al., *J. Urol.*, 2002, 168(2):542-5). In a second clinical trial, employing a combination of GM-CSF and ketoconazole in men with advanced prostate cancer, slower progression and some growth arrest of prostate cancer was reported (Ryan et al., *J. Urol.* 2007, 178(6):2372-6).

Treatment of patients with metastatic androgen-independent prostate cancer with a combination of thalidomide and GM-CSF has been shown to lead significant reductions in PSA levels (Dreicer et al., *Urol. Oncol.*, 2005, 23(2):82-86). Dr C. Myers, of the American Institute of Prostatic Diseases, has performed a large-scale clinical trial of a combination of ketoconazole, GM-CSF, transdermal estradiol and hydrocortisone with outstanding therapeutic results (Prostate Forum, C. E. Myers ed., Rivanna Health Publications Inc., 11(9):3-11 (2010), 12(1):3-6 (2011) and 12(2):1-3 (2011)). For any combined drug and immune treatment composition, it is important that the composition includes agents that target replacement of any lost, or impaired, function in other body tissues. For example, ketoconazole affects the adrenal gland and the production of hydrocortisone. The use of estrogens may be indicated to promote bone repair as bone metastatic cancer cells are killed.

Figure 1:
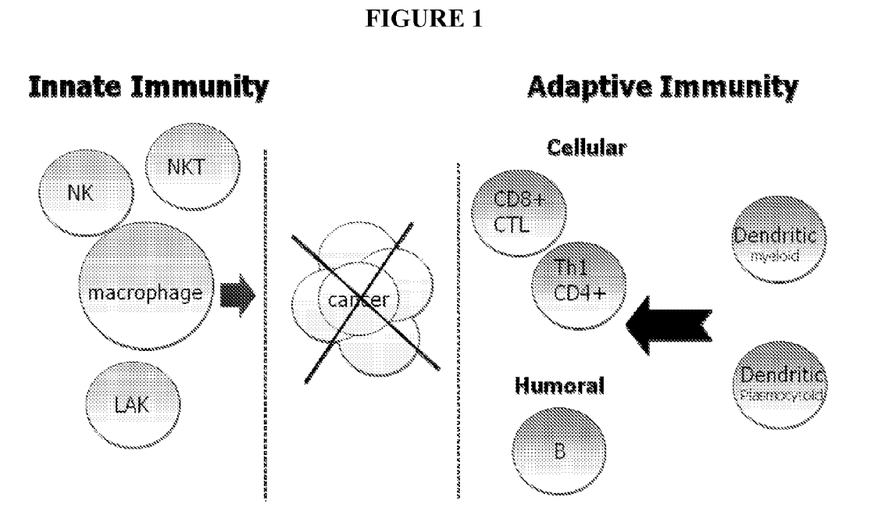
FIG. 1 illustrates the cell types that comprise the innate and adaptive immune systems, and which are believed to kill cancer cells.

The immune system is our natural defense shield providing protection from developing cancers as well as invading microorganisms. However, the immune system is also a barrier to tissue and cell transplantation as it recognizes the transplanted tissue and/or cells as foreign and, in the absence of immunosuppressant therapy, sets out to destroy such transplanted tissues and cells. The human immune system is composed of different blood cell types and their soluble products that together create a system that can sense and kill both infectious disease agents and cancer cells. As shown in FIG. 1, these cells can be divided into innate and adaptive killer cells.

While dendritic cells are innate immune cells, they are generally not killer cells and there are specialized innate killer cells capable of killing cancer cells. Innate immune cells give rise to nonspecific immunity. The innate immune response includes the following characteristics:

There is no learning, memory or lasting protective immunity;

There are a limited number of recognition molecules, or antigens, on the surface of cancer cells that the innate blood cells home to;

Once innate cells are activated, cancer cells can be destroyed within hours; and The key innate cell types are natural killer (NK) cells, natural killer T (NKT) cells and macrophages.

All cells have protein "fingerprints" on their surfaces. For white blood cells, these fingerprints are called cluster designation, or CD markers. The CD markers are assigned numbers for identification purposes, and cells are either positive or negative for these markers. These markers allow cells to be distinguished and identified. CD56 is the primary fingerprint for NK cells and NKT cells, which distinguishes them from other cells. In addition to CD56, NKT cells also carry a CD3 marker.

NK cells and NKT cells both kill cancer cells through the release of small cytoplasmic granules of proteins called perforin and granzyme that cause the target cell to die by apoptosis (programmed cell death). NK cells are named "natural killers" because they do not require activation in order to kill cells that are missing "self" markers of major histocompatibility complex (MHC) class I molecules. NKG2D is a type II transmembrane-anchored glycoprotein expressed as a disulfide-linked homodimer on the surface of all human NK cells (NK cells). Stimulation of NK cells through NKG2D triggers cell-mediated cytotoxicity. NKG2D binds to a family of ligands with structural homology to MHC class I molecules. However, unlike conventional MHC class I molecules, NKG2D ligands are frequently over expressed by tumors.

NKT cells are a subset of T cells that co-express a $\alpha\beta$ T cell receptor (TCR), but also express a variety of molecular markers that are typically associated with NK cells, such as NK1.1. They differ from conventional $\alpha\beta$ T cells in that their TCRs are far more limited in diversity. In addition, unlike conventional T cells that recognize peptide antigen presented by MHC molecules, NKT cells recognize lipid and glycolipid antigens presented by a cell membrane molecule called CD1d. NKT cells include NK1.1$^+$ and NK1.1$^-$, as well as CD4$^+$, CD4$^-$, CD8$^+$ and CD8$^-$ cells (Jerud et al., *Transfus. Med. Hemother.* 2006, 33(1):18-36; Godfrey et al., *Nat. Rev. Immunol.* 2004, 4(3):231; Vivier et al., *Nat Rev Immunol* (2004) 4(3):190-198). Invariant natural killer T (iNKT) cells are a subset of NKT cells that express high levels of, and are dependent on, the transcriptional regulator promyelocytic leukemia zinc finger (PLZF) for their development (Savage et al., *Immunity*, 2008, 29(3):391-403; Kovalovsky et al., *Nature Immunology*, 2008, 9(9):1055-64). Unlike NK cells, NKT cells are themselves killed in vivo through the interaction of CD95 (Fas) in the NKT cell membrane with CD178 (FasL) and the activation of apoptosis.

In contrast to innate immunity, adaptive immunity is learned immunity and depends mostly on B-cells and T-cells. The characteristics of the adaptive immune response include the following:

T helper cell ($T_h$ cells; also known as CD4$^+$ T cells) assist maturation of B cells into plasma cells and activation of cytotoxic T cells and macrophages. Helper T cells become activated when they are presented with peptide antigens by MHC class II molecules that are expressed on the surface of antigen presenting cells (APCs), such as dendritic cells. Once activated, they divide rapidly and secrete small proteins called cytokines that regulate or assist in the active immune response. These cells can differentiate into one of several subtypes, including $T_H1$, $T_H2$, $T_H3$, $T_H17$ or $T_{FH}$, which secrete different cytokines to facilitate a different type of immune response.

Cytotoxic T cells ($T_C$ cells or CTLs; also known as CD8$^+$ T cells) destroy virally infected cells and tumor cells. The role of the CD8$^+$ T cells is to monitor all the cells of the body, ready to destroy any that express foreign antigen fragments in their class I molecules. Cytotoxic T cells recognize their targets by binding to antigens associated with MHC class I, which is present on the surface of nearly every cell of the body.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise two subtypes: central memory T cells ($T_{CM}$ cells) and effector memory T cells ($T_{EM}$ cells). Memory cells may be either CD4$^+$ or CD8$^+$. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of $CD4^+$ regulatory T cells have been described, including the naturally occurring $T_{reg}$ cells and the adaptive $T_{reg}$ cells.

Naturally occurring $T_{reg}$ cells (also known as $CD4^+CD25^+$ $FoxP3^+$ $T_{reg}$ cells) arise in the thymus and have been linked to interactions between developing T cells with both myeloid (CD11c+) and plasmacytoid (CD123+) dendritic cells that have been activated with TSLP. Naturally occurring $T_{reg}$ cells can be distinguished from other T cells by the presence of an intracellular molecule called FoxP3.

A common feature of both prostate and breast cancer is that the phenotype of the disease varies from one patient to another. More specifically, prostate and breast cancers display very heterogeneous cellular morphologies, growth rates, responsiveness to androgen or estrogen hormones and their pharmacological blocking agents, and metastatic potential, in different individuals. This heterogeneity in cancer phenotype is reflected in the effectiveness of different treatment compositions used by physicians, in that different prostate or breast cancer phenotypes are responsive to very different drug compositions. This is a major problem for physicians when determining the best treatment protocol for individual patients. Furthermore, the advancements in diagnostic methods for both prostate and breast cancer have failed to solve the problems facing the cancer specialist. For example, current diagnostic techniques are unable to determine whether each newly diagnosed prostate or breast cancer is an indolent, non-life threatening, form of the disease, or a virulent form capable of lethality; whether the cancer is contained in the prostate or breast, or whether it will, or has metastasized; and which drug composition is likely to be most effective in treating the disease.

There thus remains a need in the art for methods that assist physicians to better select drug treatments, and in particular combination drug compositions for individual patients with prostate cancer or breast cancer, and for methods for monitoring the efficacy of treatment protocols.

SUMMARY

The present disclosure provides methods for selecting a treatment composition, or therapy, for the treatment of a cancer, such as prostate or breast cancer, in a patient wherein the treatment composition includes administering a combination of at least two components selected from two different classes of compounds. Methods for treating a patient using the selected treatment composition are also provided, together with methods for monitoring the efficacy of the treatment composition during a treatment period.

In one aspect, methods are provided for determining the efficacy of a candidate anti-cancer therapy for a specific patient diagnosed with a cancer, wherein the candidate anti-cancer therapy comprises an immune cell activating agent and an antigen display enhancing agent that is able to stimulate, or enhance, the presentation of at least one cancer-specific antigen on the surface of cancer cells. Such methods include the following steps:

(a) incubating immune cells obtained from the patient with at least one immune cell activating agent to provide activated immune cells;

(b) incubating cancer cells from an established cancer cell line with at least one antigen display enhancing agent to provide treated cancer cells; and (c) contacting the activated immune cells with the treated cancer cells and determining the ability of the activated immune cells to kill the treated cancer cells.

The ability of the activated immune cells to kill the treated cancer cells is indicative of the efficacy of the candidate anti-cancer therapy. Thus, an immune cell activating agent that is able to activate immune cells to kill treated cancer cells at a rate that is at least two times the rate of killing observed with non-activated immune cells, and/or is able to activate immune cells such that the number of treated cancer cells killed by the activated immune cells is at least 50% greater than the number of treated cancer cells killed by non-activated immune cells, can be effectively employed to treat cancer in the patient. Such immune cell activating agents can be employed either in combination with an antigen display enhancing agent or alone or in combination with one or more known cancer treatments.

Similarly, an antigen display enhancing agent that gives rise to a rate of killing of treated cancer cells by activated immune cells that is at least two times the rate of killing observed with non-treated cancer cells, and/or results in a number of treated cancer cells killed by activated immune cells that is at least 50% greater than the number of non-treated cancer cells killed by activated immune cells, can be effectively employed to treat cancer in the patient, either in combination with an immune cell activating agent or alone or in combination with one or more known cancer treatments.

The assays disclosed herein may also reveal immune suppressive properties. Thus, a candidate immune cell activating agent that is able to activate immune cells to inhibit the cytotoxic properties of innate immune cells may result in a reduction of the ability to kill treated cancer cells, for example at a rate that is at least two times lower than the rate of killing observed with non-activated immune cells, or with fewer cancer cells killed by non-activated cells. This indicates that the candidate immune cell activating agent cannot be effectively employed, either in combination with an antigen display enhancing agent or alone or in combination with one or more known cancer treatments, to treat cancer in the patient.

Similarly, a candidate antigen display enhancing agent that gives rise to a rate of killing of treated cancer cells by activated immune cells that is at least two times lower than the rate of killing observed with non-treated cancer cells cannot be effectively employed to treat cancer in the patient, either in combination with an immune cell activating agent or alone or in combination with one or more known cancer treatments.

In certain embodiments, the immune cells obtained from the patient and used in the disclosed methods are either peripheral blood mononuclear cells (PBMCs) or peripheral blood lymphocytes (PBLs) obtained, for example, from a blood sample, or immune cells obtained from a lymph node biopsy taken from the patient.

The established cancer cell line corresponds to the cancer with which the patient is inflicted. For example, when the patient is suffering from prostate cancer, the established cell line is a prostate cancer cell line; when the patient is suffering from breast cancer, the established cell line is a breast cancer cell line. As detailed below, in certain embodiments an established cancer cell line is employed that has similar properties, such as antigen expression or responsiveness to hormones, etc., to the patient's cancer cells.

In some embodiments, the immune cell activating agent activates cells of the innate immune system. In other embodiments, the immune cell activating agent activates cells of the adaptive immune system or, alternatively, cells of both the innate and adaptive immune systems. Examples of immune cell activating agents that may be successfully employed in the disclosed methods include, but are not limited to, granulocyte-macrophage colony stimulating factor (GM-CSF); granulocyte colony stimulating factor (G-CSF); inactivated mycobacterial species; components of bacterial cell walls that have adjuvant activity; and antibodies (or antigen-binding fragments thereof) that are agonists or antagonists of CD137, CD152, CD95 or CD178.

In certain embodiments, the antigen display enhancing agent is selected from the group consisting of: ketoconazole, itraconazole and fluconazole; lysophospholipid analogues (LPAs), such as alkylglycerophosphocholine, edelfosine, ilmofosine and miltefosine; amphotericin B; compounds that lower testosterone or estrogen levels including compounds that block luteinizing hormone-releasing factor, such as Zolodex® (goselerin acetate) and Lupron® (leuprolide); compounds that block testosterone action, such as Casodex® (bicalutamide), flutamide (Eulexin®), Avodart® (dutasteride), finasteride, thalidomide, Celebrex® (celecoxib), candesartan, candesartan cilexetil phenylbutyrate, atrasentan, captopril, Accutane® (isotretinoin), Vesanoid® (tretinoin), Avandia® (rosiglitazone) and Actos® (pioglitazone); compounds that block estrogen action, such as tamoxifen and aromatases; other drugs used to treat breast cancer, such as non-steroidal aromatase inhibitors (for example, letrozole and anastrozole), steroidal aromatase inhibitors (such as exemestane), selective estrogen receptor down-regulators (SERDs, such as fulvestrant); everolimus; compounds that block dihydroxy-testosterone production, such as 5α- and 5β-reductase inhibitors and abitraterone; monoclonal antibodies such as trastuzumab (Herceptin®); chemotherapeutic compounds, such as Taxotere® (docetaxel) and other taxol derivatives, and gemcitibine; and compounds that provide bone protection, such as bisphosphonates, including Aredia® (pamidronate) and Zometa® (zoledronic acid). In specific embodiments, the immune cell activating agent is GM-CSF or G-CSF and the antigen display enhancing agent is ketoconazole. Analysis of blood cells treated with Leukine® (GM-CSF) in vivo for changes in perforin levels shows that Leukine® causes major increases in perforin levels. NK and NKT cells rely mostly on perforin/granzyme-B mediated mechanisms.

In another aspect, methods for treatment of a cancer in a specific patient are provided, the methods comprising administering to the patient a combination of an immune cell activating agent and an antigen display enhancing agent, wherein the immune cell activating agent and the antigen display enhancing agent have been identified as being efficacious in the treatment of the patient's cancer using a method described herein. In certain embodiments, the treatment methods additionally comprise the administration of an agent that acts to replace at least one function that is lost due to administration of the immune cell activating agent and the antigen display enhancing agent, such as agents that assist in maintaining normal levels of vitamin D3 in the serum.

In yet a further aspect, methods for monitoring the efficacy of a treatment composition employing a combination of an immune cell activating agent and an antigen display enhancing agent are provided, such methods comprising obtaining blood samples from the patient before treatment and at various time intervals during treatment, separating PBMCs from the blood samples, incubating the PBMCs with a predetermined amount of the immune cell activating agent to provide activated immune cells, and determining the ability of the activated immune cells to kill cells from an established cancer cell line that have been treated with the antigen display enhancing agent. A decrease in the rate of killing of the treated cancer cells over time is indicative of a decrease in the efficacy of the combination treatment and a need to switch the patient to a different treatment composition.

The efficacy of the combination treatment composition can also, or alternatively, be monitored by measuring the level of at least one biomarker in the patient's blood or urine, for example, both before and during the treatment period. Examples of biomarkers that can be employed in such methods include, but are not limited to, prostate specific antigen (PSA) and other cancer specific biomarkers; blood metabolites such as hydrocortisone and serum vitamin D3; testosterone; hydroxyl-testosterone; and estrogens.

The above-mentioned and additional features of the present invention and the manner of obtaining them will become apparent, and the invention will be best understood, by reference to the following more detailed description. All references disclosed herein are hereby incorporated by reference in their entirety as if each was incorporated individually.

BRIEF DESCRIPTION OF THE DRAWINGS

The following drawings form part of the present specification and are included to further demonstrate certain aspects of the present disclosure.

DETAILED DESCRIPTION

Figure 2:
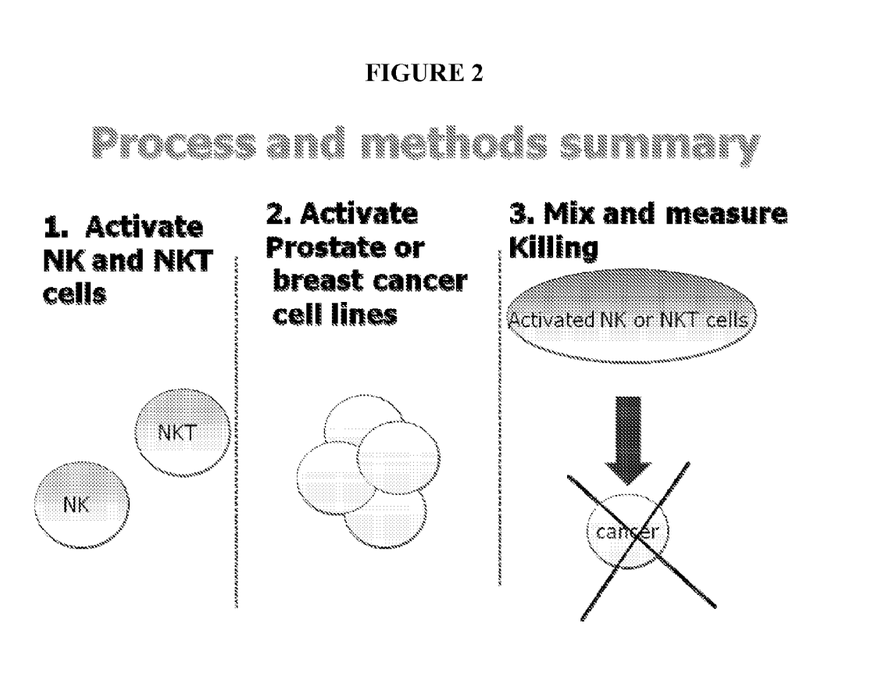
FIG. 2 is a schematic of a process and method disclosed herein.

As outlined above, the present disclosure provides methods for predicting the efficacy of a cancer treatment composition, or therapy, for a specific cancer patient, wherein the treatment composition includes two components, or compounds, selected from two different classes of compounds. A schematic of a disclosed method is shown in FIG. 2.

One of the two classes of compounds, referred to herein as immune cell activating agents or immune cell activators, is used to enhance the ability of the patient's own immune cells to kill the cancer cells. The other class of compounds, referred to herein as antigen display enhancing agents, or antigen display enhancers, is employed to increase expression and/or presentation of target antigens on the patient's cancer cells, thereby targeting the cancer cells for killing by the patient's immune cells. In certain embodiments, the treatment composition is employed to treat a patient with either prostate cancer or breast cancer, and includes the combined use of at least one compound that activates, or induces, a cytotoxic state in innate immune cells and at least one compound that induces prostate or breast cancer cells to express one or more antigenic targets recognized by the cytotoxic innate immune cells. It is believed that compounds from the two classes work synergistically, such that administration of the at least two compounds in combination results in greater killing of cancer cells than administration of either compound alone.

As used herein, the term "immune cell activating agent" or "immune cell activator" refers to an agent that is able to activate cells of the innate and/or adaptive immune systems to a cytotoxic state. In certain embodiments, the immune cell activating agent activates cells of the innate immune system, such as NK and NKT cells. In other embodiments, the immune cell activators employed in the present methods also, or alternatively, activate cytotoxic T cells of the adaptive immune system.

Examples of immune cell activators that are able to activate cells of the innate and/or adaptive immune systems to a cytotoxic state include, but are not limited to: biologics; inactivated microorganisms; cell wall components of microorganisms; proteins, carbohydrates and other agents produced through using genetic engineering technology; antibodies and antigen-binding fragments thereof; and synthetic chemical compounds. In certain embodiments, the immune cell activators are selected from the group consisting of: cytokines, such as granulocyte-macrophage colony stimulating factor (GM-CSF; Leukine®) and granulocyte-colony stimulating factor (G-CSF; Neupogen®); inactivated bacteria, such as Bacillus Calmette-Guerin (BCG) or other mycobacterial species; components of bacterial cell walls that have adjuvant activity, such as PVAC (U.S. Pat. No. 5,985,287), AVAC (U.S. Pat. No. 6,350,457) and muramyl peptides; and antibodies (or antigen binding fragments thereof) that are agonists or antagonists of CD137 (4-1BB receptor), CTLA4 (cytotoxic T-lymphocyte antigen 4; also known as CD152), CD95 (Fas) and CD178 (Fas ligand).

As used herein, the term "antigen display enhancing agent" or "antigen display enhancer" refers to an agent that is able to increase and/or induce the expression and/or presentation of antigens on the surface of cancer cells that act as targets for cells of the innate and/or adaptive immune systems, thereby guiding cytotoxic immune cells to the cancer cells which in turn leads to killing of the cancer cells by the cytotoxic immune cells. The antigen display enhancing agents target metabolic processes that result in antigenic changes in the structure and/or composition of the surface membrane of cancer cells, such as prostate cancer or breast cancer cells.

In certain embodiments, the antigen display enhancing agents disrupt membrane lipid metabolism in cancer cells but generally not in non-cancer cells, resulting in the presentation of lipid, phospholipid and/or glycolipid antigens by CD1d which in turn are recognized by cytotoxic NKT and/or NK cells, leading to killing of the cancer cells by the cytotoxic NKT and/or NK cells. In other embodiments, metabolic processes are targeted for disruption such that, for example, events generally found in biochemical pathways that are involved in cellular apoptotic processes are partially or completely activated. An incomplete state of apoptosis in cancer results in changes in cell surface lipids or phospholipids.

Compounds that can be employed as antigen display enhancers include, but are not limited to: lipid targeting compounds, such as ketoconazole, itraconazole and fluconazole; lysophospholipid analogues (LPAs), such as alkylglycerophosphocholine, edelfosine, ilmofosine and miltefosine; amphotericin B; compounds that lower testosterone or estrogen levels including compounds that block luteinizing hormone-releasing factor, such as Zolodex® (goselerin acetate) and Lupron® (leuprolide); compounds that block testosterone action, such as Casodex® (bicalutamide), flutamide (Eulexin®), Avodart® (dutasteride), finasteride, thalidomide, Celebrex® (celecoxib), candesartan, candesartan cilexetil phenylbutyrate, atrasentan, captopril, Accutane® (isotretinoin), Vesanoid® (tretinoin), Avandia® (rosiglitazone) and Actos® (pioglitazone); compounds that block estrogen action, such as tamoxifen and aromatases; other drugs used to treat breast cancer, such as non-steroidal aromatase inhibitors (for example, letrozole and anastrozole), steroidal aromatase inhibitors (such as exemestane), selective estrogen receptor down-regulators (SERDs, such as fulvestrant); everolimus; compounds that block dihydroxy-testosterone production, such as 5α- and 5β-reductase inhibitors and abitraterone; monoclonal antibodies such as trastuzumab (Herceptin®); chemotherapeutic compounds, such as Taxotere® (docetaxel) and other taxol derivatives, and gemcitibine; and compounds that provide bone protection, such as bisphosphonates, including Aredia® (pamidronate) and Zometa® (zoledronic acid).

Certain compounds that alter membrane composition and structure, such as ketoconazole and lysophospholipid analogues (LPAs), have also been shown to have anti-tumor activity. Ketoconazole has inhibitory activity in fungii and other microorganisms, including *Staphylococcus aureus, Plasmodium falciparum, Trypanosoma cruzi* and *Leishmania tropica*. The mechanism for the inhibitory activity against these diverse organisms is related to alterations in lipid metabolism. Specifically, ketoconazole appears to exert its antifungal activity through inhibition of lanosterol demethylation. This blocks the synthesis of ergosterol, the major sterol component of the fungal cell membrane. In mammalian cells, ketoconazole also inhibits lanosterol demethylation, with a subsequent decrease in the biosynthesis of cholesterol, the major sterol component of mammalian cell membranes. In addition, ketoconazole interferes with cellular fatty acid and phospholipid biosynthesis (Borgers, M. *Rev. Infect. Dis.* 1980, 2:520-539: Bulchenauer, H. *Pestic. Biochem. Physiol.* 1978, 8:15-25; Gravestock, M. B., and J. Riley. *Annu. Rep. Med. Chem.* 1984, 19:127-136; Hall, I. H., and G. Carlson. *J. Med. Chem.* 1976, 19:1257-1261; McBride et al. *J. Antimicrob. Chemother.* 2007, 60(3): 521-525; Luque-Ortega et al. *Agents Chemother.* 2007, 51(4): 1327-1332; Santa-Rita et al., *J. Antimicrob. Chemother.* 2005, 55(5): 780-784; Miettinen T A, *J. Lipid Res.* 1988, 29 43-51; Santa-Rita et al. *J. Antimicrob. Chemother.* 2004, 54(4): 704-710).

Leukine® (GM-CSF) and ketoconazole combine to kill prostate cancer cells and not normal body cells. Ketoconazole may also induce a partial state of apoptosis in cancer cells (through activation of the Fas pathway), but not in normal cells. These partial apoptotic changes yield target antigens for cells of the innate immune system that are sufficient for the immune cells to complete killing of the cancer cells.

The antifungal agent amphotericin B also exerts its antifungal effect by binding to sterol components in the fungal cell membrane, which results in increased permeability of the membrane. Amphotericin B has been used in combination with acyclovir to further increase the efficacy of acyclovir action.

Other compounds that induce membrane lipid changes include lysophospholipid analogues shown to display anti-tumor activity, such as alkylglycerophosphocholine, edelfosine, the thioether substituted phosphatidylcholine analogue ilmofosine, and the alkylphosphocholine miltefosine.

Using the disclosed methods, a preferred treatment composition for a given patient is determined by selecting compounds from a panel of immune cell activators and a panel of antigen display enhancers based on the results of an in vitro assay using immune cells isolated from the patient's blood or lymph nodes. In certain embodiments, the assay takes advantage of the fact that cytotoxicity of innate immune cells for cancer cells is not restricted by histo-incompatibility barriers, such as those seen with cytotoxic cells of the adaptive immune system. As discussed above, NKT cells of the innate immune system rapidly carry out killing functions in response to presentation of lipid and/or glycolipid antigens. Killing of target cancer cells by both NK and NKT cells does not require a state of histocompatibility between the immune cells and the tumor cells, and therefore a patient's blood cells can be screened for cytotoxic activity against cancer cells using histo-incompatible tumor cell lines maintained in tissue culture long-term as targets in an in vitro assay.

In one aspect, methods are provided for determining the efficacy of a candidate anti-cancer therapy for a specific patient, the method including the steps of: (a) isolating peripheral blood mononuclear cells (PBMCs) from a blood sample taken from the patient or obtaining lymph node cells from the patient; (b) incubating the PBMCs or lymph node cells with at least one immune cell activating agent to provide activated immune cells; (c) incubating cells from an established cancer cell line with at least one antigen display enhancing agent to provide treated cancer cells, wherein the cancer cell line corresponds to the type of cancer with which the patient is inflicted; and (d) contacting the activated immune cells with the treated cancer cells and determining the ability of the activated immune cells to kill the treated cancer cells. A level of killing greater than two times the level observed with non-activated immune and/or non-treated cancer cells indicates that a combination of the immune cell activating agent and the antigen display enhancing agent can be effectively employed in a treatment composition for the patient.

As used herein, the term "established cell line" refers to a cell line that has been stably maintained in cell culture for a period of time. The established cancer cell line preferably corresponds to the type of cancer with which the patient is inflicted, i.e. the established cell line has characteristics that are similar to those of the patient's cancer cells. For example, immune cells from a patient diagnosed with prostate cancer will be tested against a prostate cancer cell line, while immune cells from a patient diagnosed with breast cancer will be tested against a breast cancer cell line. In the case of both prostate and breast cancer, the established cell line can be further matched, where possible, with the patient's cancer cells. For example, if a breast cancer patient's cancer cells express HER2, the patient's immune cells will be tested against an established cancer cell line that also expresses HER2; if a prostate cancer patient's cancer cells are androgen-independent, the patient's immune cells will be tested against androgen-dependent and androgen-independent cell lines.

More specifically, in a first step, blood samples from a prostate or breast cancer patient are obtained and peripheral blood mononuclear cells (PBMCs) prepared for use immediately or after storage at low temperatures. In one embodiment, this is achieved by drawing blood samples (for example, 10 ml) intravenously from a patient and isolating PBMCs by density gradient centrifugation. The PBMC are then used fresh, or stored in 90% serum and 10% dimethyl sulfoxide mixtures and frozen at −80° C.

In a second step, the PBMCs (either fresh, or previously frozen and then thawed) are subsequently placed in cell tissue culture and mixed with one or more immune cell activators. In certain embodiments, the PBMCs are incubated with one or more immune cell activators for periods of six to 72 hours.

Following incubation with the immune cell activator(s), the activation level and/or cytotoxicity of immune cells, such as NK and NKT cells, in the PBMCs are then determined. Assays for evaluating NK and NKT cell activation and/or function are well known in the art and include, for example, production of IL4 and/or IFN-γ (as determined by IFN-γ ELISpot, for example) and ex vivo NKT cell proliferation. Panels of fluorescently labeled tags that bind selectively to different cell types can also be used to analyze resting and activated NKT cells, myeloid dendritic cells and monocyte numbers/phenotype. Assays for quantitative changes can be performed as immune cell activators, such as GM-CSF, are added to the cell populations. Approximately $1 \times 10^6$ frozen PBMCs per patient, or per time point, are required to enumerate and phenotype the circulating NK, NKT, monocytes, dendritic cells, and another $1-2 \times 10^6$ cells are required to evaluate cell function.

In a third step, following incubation with one or more immune cell activators, the PBMCs are harvested by centrifugation and assayed quantitatively for their specific ability to kill prostate cancer cells or breast cancer cells that have been treated to stimulate and/or enhance the presentation of cancer specific antigens as detailed below, compared to the ability of non-activated PBMC's for the cancer patient and/or PBMCs from normal donors to kill treated and/or non-treated cancer cells. The ability of the activated PBMCs to kill cells can be determined, for example, by flow cytometry using staining reagents that distinguish between viable and dead cells.

Cancer cells from established cell lines are treated in order to stimulate and/or enhance the presentation of cancer-specific antigens on the surface of the cancer cells as follows. Human prostate cancer cell lines or breast cancer cell lines, derived from publicly available cell lines (for example from the American Tissue Type Collection or similar reputable cell storage banks) are maintained in standard tissue culture media under standard conditions, such as RPMI 1640 supplemented with 5-10% human serum at 37° C. in an atmosphere of 5% carbon dioxide gas mixtures. The cancer cell lines are then incubated with one or more antigen display enhancers.

Following the identification of a preferred therapy including a combination of immune cell activator and antigen display enhancer for a specific patient, the immune cell activator and antigen display enhancer are administered to the patient using administration routes, dosages and frequencies of administration well known to those of skill in the art, including those commonly employed for such compounds. The immune cell activator and antigen display enhancer can be administered simultaneously or sequentially, and can be administered individually or in a single composition. The preferred therapy can be administered in combination with one or more treatments currently employed for the treatment of cancer, such as, but not limited to, radiotherapy.

As used herein the term "patient" refers to a subject who has previously been diagnosed with a cancer. As used herein, the term "subject" refers to a mammal, preferably a human. The disclosed methods can be used to select treatment compositions for, and/or to treat, patients diagnosed with prostate cancer, including patients with early stage prostate cancer; patients who have had surgery to remove the prostate (radical prostatectomy); patients who have undergone radiation treatment for prostate cancer; patients who are undergoing, or have completed, androgen ablation therapy; patients whose cancer has become resistant to hormone ablation therapy; and patients who are undergoing, or have had, chemotherapy. The disclosed methods can also be employed to select treatment compositions for, and/or to treat, patients diagnosed with breast cancer, including patients who have had surgery to remove one or more breasts (radical mastectomy); patients who are undergoing or have had radiation treatment; patients who are undergoing or have completed estrogen ablation therapy; patients whose cancer has become resistant to estrogen ablation therapy; and patients who are undergoing or have had chemotherapy. It will also be apparent to those of skill in the art that the disclosed methods can be employed to select treatment compositions and/or to treat, patients inflicted with other cancers.

The methods described herein can also be employed to monitor the effectiveness of treatment compositions for individual cancer patients. In particular, the disclosed methods can be used to monitor treatment compositions in which the patient is receiving a combination of an immune cell activator and an antigen display enhancer. Specifically, blood samples are drawn intravenously from the patient before treatment, at various time points during treatment, and after treatment. PBMCs are isolated from the blood samples by density gradient centrifugation, and then either used fresh, or stored in 90% serum and 10% dimethyl sulfoxide mixtures and frozen at −80° C. for later use. The ability of the PBMCs to kill prostate cancer or breast cancer cells treated with the antigen display enhancer employed in the treatment composition can be determined as detailed above. A significant reduction in the ability of the PBMCs to kill the treated cancer cells indicates that the treatment composition may no longer be effective and that the patient may benefit from a change in the composition, such as changing one of the compounds being administered.

The levels of known cancer-specific biomarkers, such as PSA, may also be monitored to provide an indication of the effectiveness of the treatment composition. The blood samples may also be analyzed to determine the level of immune health markers, such as the number of total white cells (including B cells, NK cells, and NK T cells); naive CD4+ and CD8+ cells; memory CD4+ CD45RO+ cells and CD8+ CD45RO+ cells; myeloid suppressor cells (CD45−, CD14lo, CD33+, CD34−, lineage-negative (Lin−), CD206+ and HLADR+ cells); and T regulator cells (FOX3+ cells).

EXAMPLES

The following examples are included to demonstrate exemplary embodiments of the present disclosure.

Example 1

As detailed below, significant changes in peripheral blood immune cell subset analysis in a prostate cancer patient were observed before and after combined Leukine® and ketoconazole treatment, compared to peripheral blood immune cell subset analysis of a healthy male. In all the studies discussed below, peripheral blood immune subset analyses were performed using blood from the same prostate cancer patient and the same healthy male donor.

A 66 year old male, diagnosed 6 years previously with metastatic prostate cancer and refractory to hormone ablation therapy, had ceased all treatment for three months. At that time his serum PSA level was 509 ng/ml. The patient commenced treatment with daily injections of 0.5 mg Leukine® and administration of 400 mg ketoconazole every eight hours. Blood samples were taken immediately prior to start of treatment and after three weeks of treatment. White cells were harvested from the blood samples and analyzed as described below. As a control, blood samples were taken from a healthy 40 year old male donor with a PSA level less than 0.1 ng/ml at the same time points and analyzed in the same manner as the blood samples from the patient.

Whole human blood was collected in green-topped heparin tubes. Blood was transferred to 50 mL Falcon tubes in a sterile hood, and diluted with an equal volume of sterile, pre-warmed phosphate buffered saline (PBS). Diluted blood was then carefully layered over Ficoll™ (Ficoll-Paque™; Amersham Pharmacia Catalog #17-1440-03) at up to 30 mL diluted blood over 15 mL Ficoll™, and tubes were centrifuged at 1800 rpm for 15 min with no brake to ensure gentle deceleration.

After centrifugation, cells in the buffy coat layer at the Ficoll™ interface were harvested using a sterile disposable pipette and washed into a large volume of sterile, pre-warmed PBS. Cells were then pelleted by spinning at 1000 rpm for 5 min. Wash supernatant was discarded, cells resuspended in 10 mL sterile, pre-warmed PBS, and counted. Cell yield should be $1 \times 10^6$ cells per mL of whole blood collected.

Figure 3:
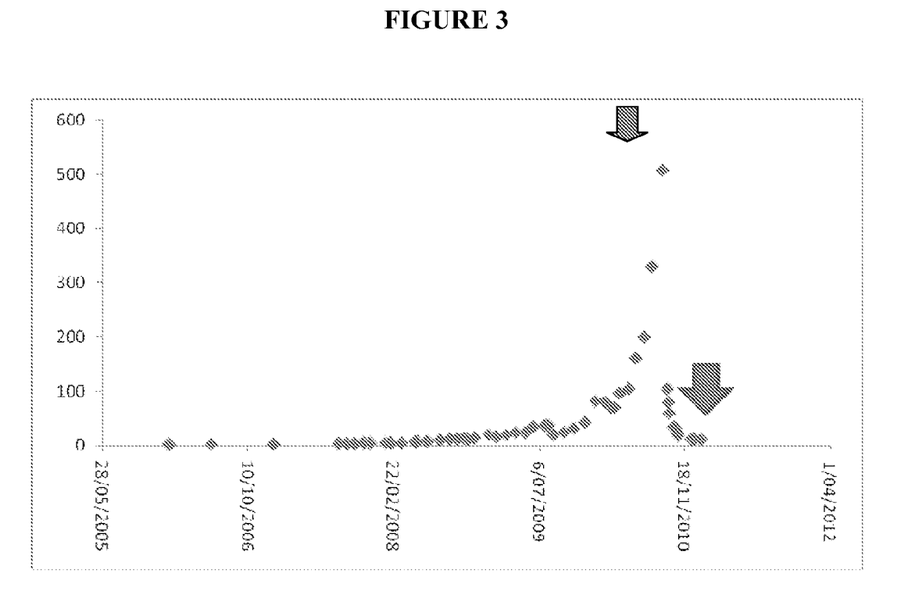
FIG. 3 shows the change in PSA levels in a prostate cancer patient before and during treatment with a combination of Leukine® (GM-CSF) and ketoconazole.

After four months of treatment, the patient's PSA levels had decreased to 9.8 ng/ml. The time course of decreasing serum prostate antigen levels in the prostate cancer patient both before and after treatment with Leukine® and ketoconazole is shown in FIG. 3, with the first arrow showing the start of treatment (PSA of 509 ng/ml) and the second arrow showing the end of the 4 month treatment period (PSA of 9.8 ng/ml).

Figure 4:
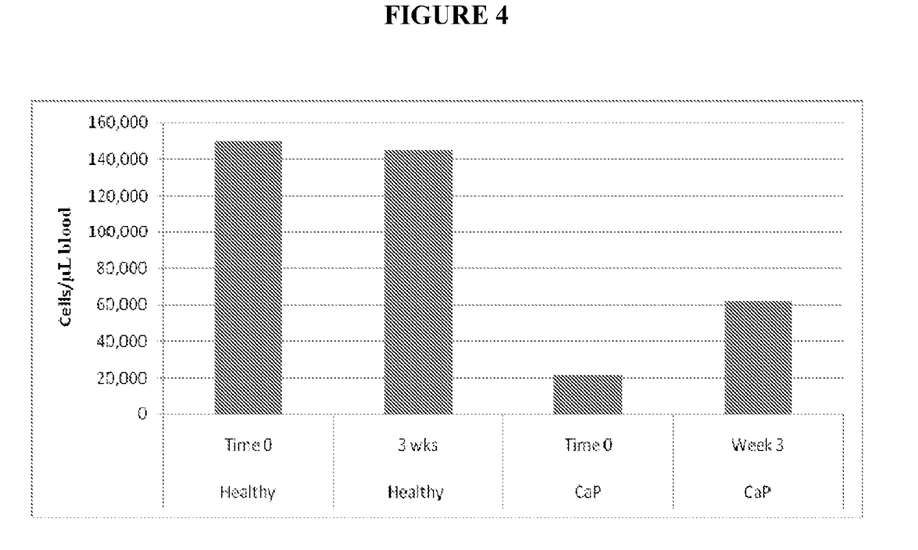
FIG. 4 shows the numbers of naïve CD4+ T cells in the blood of a prostate cancer patient before and three weeks after treatment with a combination of Leukine® and ketoconazole, compared with the number of CD4+ T cells in the blood of a healthy donor.

FIG. 4 shows a comparison of numbers of naïve CD4+ T cells in the blood of the prostate cancer patient (referred to in the Figures as CaP) after treatment with Leukine® and ketoconazole, with those in the blood of the untreated healthy donor. The absolute numbers of naïve CD4+ T cells were much higher in the blood of the healthy donor; however the absolute numbers of naïve CD4+ T cells increased in the blood of the prostate cancer patient after three weeks of treatment with Leukine® and ketoconazole.

Figure 5:
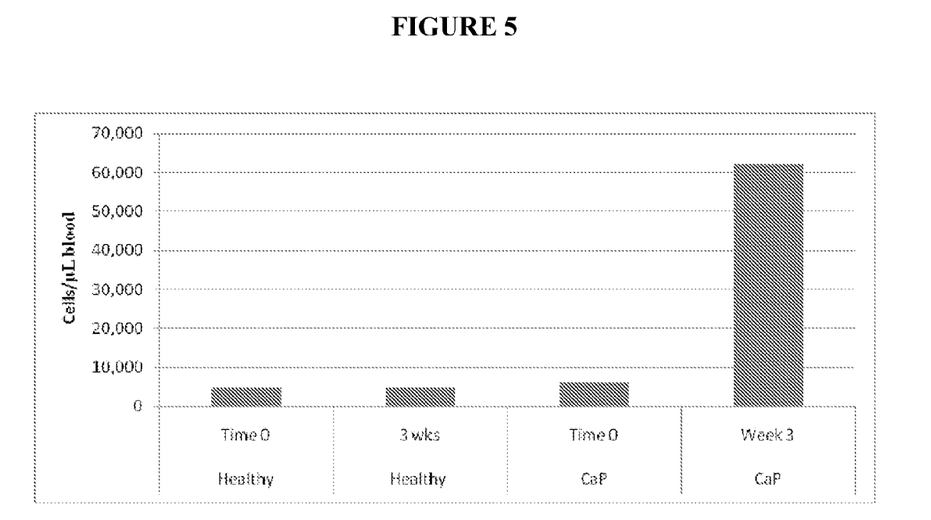
FIG. 5 shows the numbers of NKT cells in the blood of a prostate cancer patient before and three weeks after treatment with a combination of Leukine® and ketoconazole, compared with the number of NKT cells in the blood of a healthy donor.

FIG. 5 shows a comparison of the numbers of NKT cells in the blood of the prostate cancer patient after treatment with Leukine® and ketoconazole with those in the blood of the untreated healthy donor. The absolute numbers of NKT cells did not change in the blood of the healthy donor; however the absolute numbers of NKT cells increased in the blood of the prostate cancer patient following three weeks of treatment with Leukine® and ketoconazole.

Figure 6A:
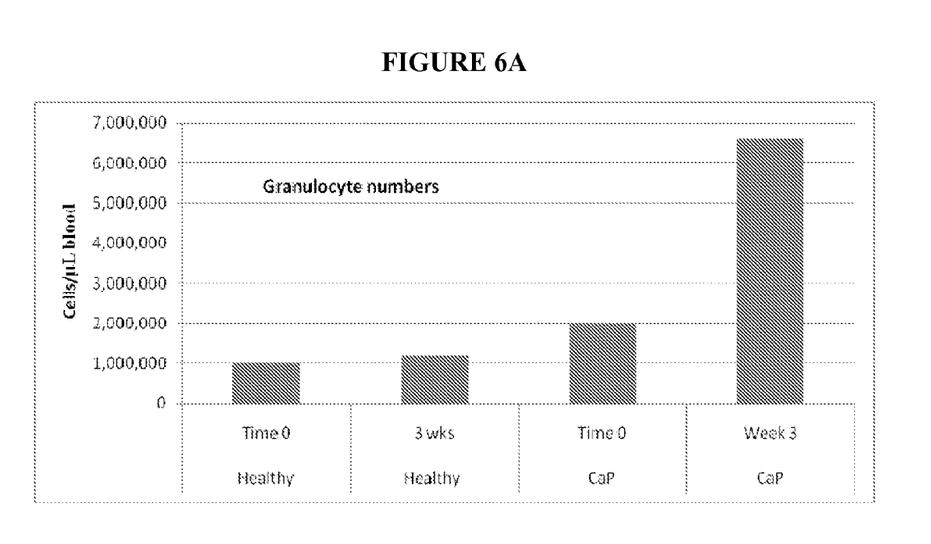
FIGS. 6A-C show the numbers of granulocytes, HLA-DR$^{hi}$ monocytes as a percentage of the total number of CD14+ cells, and CD206$^{hi}$ monocytes as a percentage of the total number of CD14+ cells, respectively, in the blood of a prostate cancer patient before and three weeks after treatment with a combination of Leukine® and ketoconazole, compared with the number of those cells in the blood of a healthy donor.
Figure 6B:
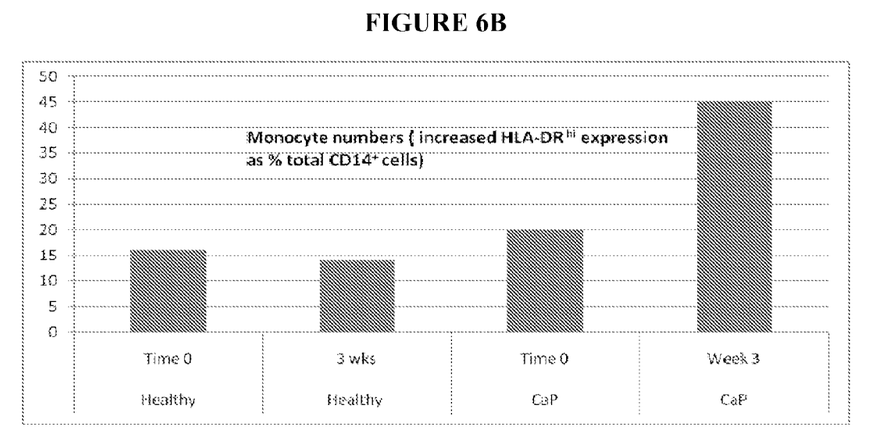
Figure 6C:
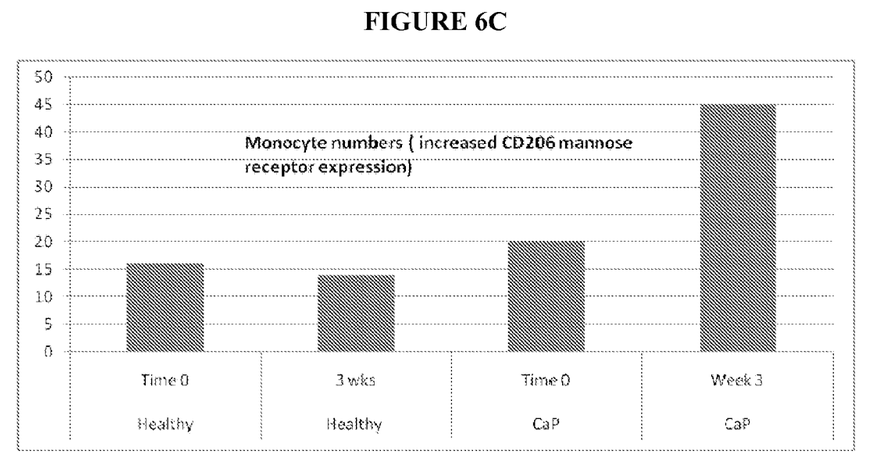

FIGS. 6A-C demonstrate myeloid cell activation in the blood of the healthy donor and in the blood of the prostate cancer patient after treatment with Leukine® and ketoconazole. The absolute numbers of granulocytes were found to increase in the blood of the prostate cancer patient after three weeks of treatment with Leukine® and ketoconazole (FIG. 6A). In addition, both HLA-DR$^{hi}$ monocytes as a percentage of the total number of CD14+ cells (FIG. 6B) and CD206$^{hi}$ monocytes (mannose receptor) as a percentage of the total number of CD14+ cells (FIG. 6C) were found to have increased following three weeks of treatment with Leukine® and ketoconazole.

Figure 7A:
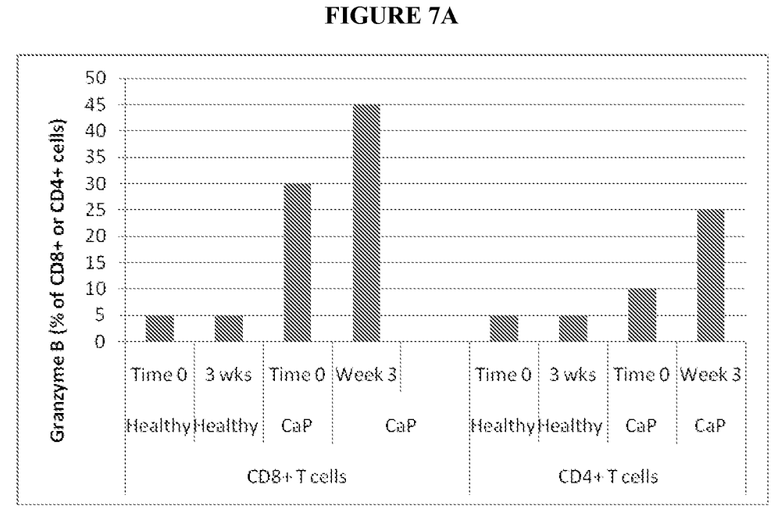
FIGS. 7A and 7B show that elevated numbers of granzyme B-expressing CD8+ T cells, or CD4+ T cells (FIG. 7A) and granzyme B-expressing total NK cells (FIG. 7B) were observed in the blood of a prostate cancer patient following three weeks of treatment with a combination of Leukine® and ketoconazole compared with the numbers found in the blood of a healthy donor.
Figure 7B:
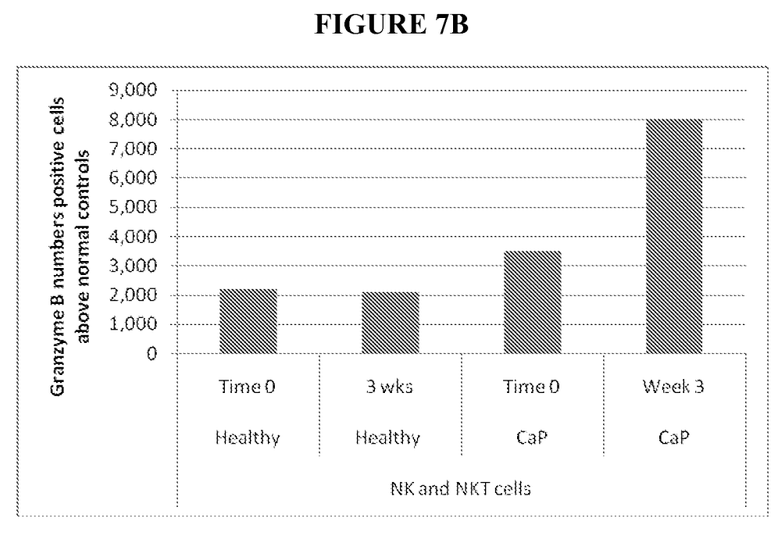
Figure 8:
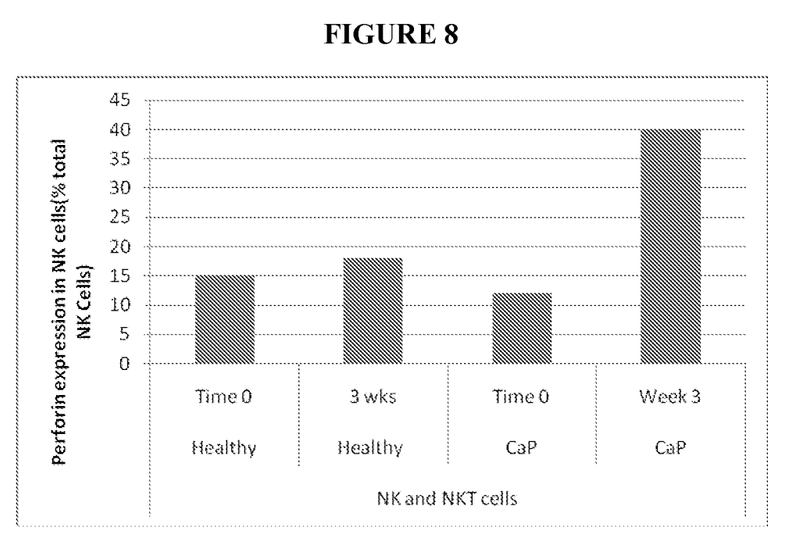
FIG. 8 shows that elevated levels of perforin-expressing total NK cells were observed in the blood of a prostate cancer patient following three weeks of treatment with a combination of Leukine® and ketoconazole compared with the numbers found in the blood of a healthy donor.

As shown in FIGS. 7A and B, elevated levels of granzyme B-expressing CD8+ T cells, CD4+ T cells and total NK cells were found in the blood of the prostate cancer patient after three weeks of treatment with Leukine® and ketoconazole. In addition, as shown in FIG. 8, elevated levels of perforin-expressing total NK cells were observed in the blood of the prostate cancer patient following three weeks of treatment with Leukine® and ketoconazole. Release of granzyme B and perforin by NK cells is known to lead to apoptosis of targeted cells.

Example 2

The ability of activated immune cells to kill cancer cells is assayed as described below.

A flow cytometer is used to measure fluorescence simultaneously at several different wavelengths, in addition to light scatter in two directions, at rates of thousands of cells per second. To distinguish live from dead cells, several approaches are employed, based on the use of vital dyes. Examples of such dyes include: nucleic acid-binding fluorescence dyes that are excluded by intact cells and admitted by dead cells, such as ethidium bromide, propidium iodide, and SYTOX™ Green; and molecules which enter live cells and react with intracellular esterases to yield a fluorescence product which is retained as long as the plasma membrane remains intact, such as fluorescein acetate and carboxyfluorescein diacetate.

The assay is performed in three steps:

A. For the activation of cytotoxic activity in innate immune cells, PBLs or lymph node cells are incubated in vitro at cell concentrations of $10^5$ to $10^6$ cells/ml for varying times from 0 to 72 hours with at least one immune cell activator, such as Leukine®, in the range of 1 ng/ml to 100 µg/ml. As controls, PBLs or lymph node cells are incubated in vitro at cell concentrations between $10^5$ and $10^6$ cells/ml for varying times from 0 to 72 hours with no added immune activator. At the end of a specified period, cells are harvested by centrifugation, recovered cell numbers determined and then titrated into tubes containing cancer target cells.

B. Cancer target cells are prostate or breast cancer cells from continuous cell lines maintained in culture. For the cytotoxic assay, cancer cells are harvested by centrifugation, recovered cell numbers determined and the cells incubated in vitro at cell concentrations of $10^5$ to $10^6$ cells/ml for varying times from 0 to 72 hours with at least one antigen display enhancer, such as ketoconazole, in the range of 1 ng/ml to 100 µg/ml. At the end of a specified period, cells are harvested by centrifugation, recovered cell numbers determined and the cells mixed with a vital dye. The cells are then titrated into tubes for mixing with the activated PBLs or lymph node cells.

C. For the killing assay, $10^6$ stained cancer cells are added. Control or activated PBLs or lymph node cells are titrated into tubes in concentrations ranging from $10^4$ to $5\times10^6$ cells. The mixtures are incubated at 37° C. for 60 minutes and the cells are examined by flow cytometry to determine the number of viable cancer cells remaining.

While this invention has been described in conjunction with the specific embodiments outlined above, it is evident that many alternatives, modifications and variations will be apparent to those skilled in the art. Accordingly, the embodiments of this disclosure as set forth above are intended to be illustrative, not limiting. Various changes may be made without departing from the spirit and scope of this disclosure as defined in the following claims. All publications referenced herein are incorporated herein by reference as though fully set forth.

What is claimed is:

1. A method for determining the efficacy of a candidate anti-prostate cancer therapy for a patient diagnosed with prostate cancer wherein the candidate anti-prostate cancer therapy comprises an immune cell activating agent and an antigen display enhancing agent that is able to stimulate or enhance the presentation of a cancer-specific antigen on the surface of prostate cancer cells, the method comprising:
   (a) incubating immune cells obtained from the patient with the immune cell activating agent to provide activated immune cells;
   (b) incubating prostate cancer cells from an established prostate cancer cell line with the antigen display enhancing agent, thereby providing treated prostate cancer cells;
   (c) contacting the activated immune cells with the treated prostate cancer cells; and
   (d) determining the ability of the activated immune cells to kill the treated prostate cancer cells,
   wherein the ability of the activated immune cells to kill the treated prostate cancer cells is indicative of the efficacy of the candidate anti-prostate cancer therapy.

2. The method of claim 1, wherein the immune cell activating agent activates cells of the innate immune system.

3. The method of claim 1, wherein the immune cell activating agent is selected from the group consisting of granulocyte-macrophage colony stimulating factor (GM-CSF); granulocyte colony stimulating factor (G-CSF); inactivated mycobacterial species components of bacterial cell walls that have adjuvant activity; and antibodies, or antigen-binding fragments thereof, that are agonists or antagonists of CD137, CD152, CD95 or CD178.

4. The method of claim 1, wherein the antigen display enhancing agent activates an apoptotic process in the prostate cancer cells.

5. The method of claim 1, wherein the antigen display enhancing agent causes perturbation of cell lipid and cholesterol metabolism thereby altering membrane structures on the prostate cancer cells.

6. The method of claim 1, wherein the antigen display enhancing agent is selected from the group consisting of: lipid targeting compounds; ketoconazole; itraconazole; fluconazole; alkylglycerophosphocholine; edelfosine; ilmofosine; miltefosine; amphotericin B; compounds that lower testosterone or estrogen levels; compounds that block luteinizing hormone-releasing factor; goselerin acetate; leuprolide; compounds that block testosterone action; bicalutamide; flutamide; dutasteride; finasteride; thalidomide; celecoxib; candesartan; candesartan cilexetil phenylbutyrate; atrasentan; captopril; isotretinoin; tretinoin; rosiglitazone; pioglitazone; tamoxifen; aromatases; non-steroidal aromatase inhibitors; letrozole; anastrozole; steroidal aromatase inhibitors; exemestane; selective estrogen receptor down-regulators (SERDs); fulvestrant; everolimus; compounds that block dihydroxy-testosterone production; 5α- and 5β-reductase inhibitors; abitraterone; trastuzumab; chemotherapeutic compounds; docetaxel; gemcitibine; bisphosphonates; pamidronate; and zoledronic acid.

7. The method of claim 1, wherein the immune cells are isolated from a biological sample selected from the group consisting of: blood; and lymph node tissue.

8. A method for monitoring the efficacy of an anti-prostate cancer therapy in a patient diagnosed with prostate cancer, wherein the anti-prostate cancer therapy comprises an immune cell activating agent and an antigen display enhancing agent that is able to stimulate or enhance the presentation of a cancer-specific antigen on the surface of prostate cancer cells, the method comprising:
- (a) incubating a first plurality of immune cells obtained from the patient prior to treatment with the immune cell activating agent to provide activated immune cells;
- (b) incubating prostate cancer cells from an established prostate cancer cell line with the antigen display enhancing agent, thereby providing treated prostate state cancer cells;
- (c) contacting the activated immune cells with the treated prostate cancer cells and determining the ability of the activated immune cells to kill the treated prostate cancer cells; and
- (d) repeating steps (b)-(c) with a second plurality of immune cells obtained from the patient at a subsequent time interval following administration of the anti-prostate cancer therapy, wherein a reduction in the ability of activated immune cells prepared from the second plurality of immune cells to kill the treated prostate cancer cells compared to the ability of activated immune cells prepared from the first plurality of immune cells to kill the treated prostate cancer cells is indicative of a reduction in the efficacy of the anti-prostate cancer therapy.

9. The method of claim 8, wherein the immune cell activating agent activates cells of the innate immune system.

10. The method of claim 8, wherein the immune cell activating agent is selected from the group consisting of: granulocyte-macrophage colony stimulating factor (GM-CSF); granulocyte colony stimulating factor (G-CSF); inactivated mycobacterial species; components of bacterial cell walls that have adjuvant activity; and antibodies, or antigen-binding fragments thereof, that are agonists or antagonists of CD137, CD152, CD95 or CD178.

11. The method of claim 8, wherein the antigen display enhancing agent activates an apoptotic process in the prostate cancer cells.

12. The method of claim 8, wherein the antigen display enhancing agent causes perturbation of cell lipid and cholesterol metabolism thereby altering membrane structures on the prostate cancer cells.

13. The method of claim 1, wherein the antigen display enhancing agent is selected from the group consisting of: lipid targeting compounds; ketoconazole; itraconazole; fluconazole; alkylglycerophosphocholine; edelfosine; ilmofosine; miltefosine; amphotericin B; compounds that lower testosterone or estrogen levels; compounds that block luteinizing hormone-releasing factor; goselerin acetate; leuprolide; compounds that block testosterone action; bicalutamide; flutamide; dutasteride; finasteride; thalidomide; celecoxib; candesartan; candesartan cilexetil phenylbutyrate; atrasentan; captopril; isotretinoin; tretinoin; rosiglitazone; pioglitazone; tamoxifen; aromatases; non-steroidal aromatase inhibitors; letrozole; anastrozole; steroidal aromatase inhibitors; exemestane; selective estrogen receptor down-regulators (SERDs); fulvestrant; everolimus; compounds that block dihydroxy-testosterone production; $5\alpha$- and $5\beta$-reductase inhibitors; abitraterone; trastuzumab; chemotherapeutic compounds; docetaxel; gemcitibine; bisphosphonates; pamidronate; and zoledronic acid.

14. The method of claim 8, further comprising monitoring levels of at least one prostate cancer specific biomarker and/or the levels of at least one marker of immune health in the patient.

15. The method of claim 8, wherein the immune cells are isolated from a biological sample selected from the group consisting of: blood; and lymph node tissue.

* * * * *

UNITED STATES PATENT AND TRADEMARK OFFICE
CERTIFICATE OF CORRECTION

| | | |
|---|---|---|
| PATENT NO. | : 8,784,795 B2 | Page 1 of 1 |
| APPLICATION NO. | : 13/935355 | |
| DATED | : July 22, 2014 | |
| INVENTOR(S) | : James D. Watson and Richard Llewellyn Sydney Foster | |

It is certified that error appears in the above-identified patent and that said Letters Patent is hereby corrected as shown below:

In the Claims

Column 17, line 11, claim 8, replace "treated prostate state cancer" with --treated prostate cancer--

Column 18, line 10, claim 13, replace "The method of claim 1" with --The method of claim 8--

Signed and Sealed this
Seventeenth Day of February, 2015

Michelle K. Lee
*Deputy Director of the United States Patent and Trademark Office*